United States Patent [19]

Bosche et al.

[11] 4,017,494
[45] Apr. 12, 1977

[54] CATALYST FOR THE MANUFACTURE OF TRIETHYLENEDIAMINE

[75] Inventors: Horst Guenter Bosche, Speyer; Karl Baer, Weinheim; Kurt Schneider, Bad Durkheim, all of Germany

[73] Assignee: BASF Aktiengesellschaft, Ludwigshafen, Germany

[22] Filed: Sept. 3, 1975

[21] Appl. No.: 609,953

[30] Foreign Application Priority Data

Sept. 7, 1974 Germany ............................ 2442929

[52] U.S. Cl. ............................................ 260/268 T
[51] Int. Cl.$^2$ ........................................ C07D 295/02
[58] Field of Search ................................ 260/268 T

[56] References Cited

UNITED STATES PATENTS 3,157,657 11/1964 Brader, Jr. ...................... 260/268 T
3,297,701 1/1967 Brader et al. ................... 260/268 T

*Primary Examiner*—Donald G. Daus
*Assistant Examiner*—Jose Tovar
*Attorney, Agent, or Firm*—Johnston, Keil, Thompson & Shurtleff

[57] ABSTRACT

A gas phase process for the production of triethylenediamine or 1,4-diaza-bicyclo-(2,2,2)-octane from N,N'-dihydroxyethylpiperazine, wherein aluminum oxide is used as a catalyst.

5 Claims, 1 Drawing Figure

U.S. Patent      April 12, 1977      4,017,494
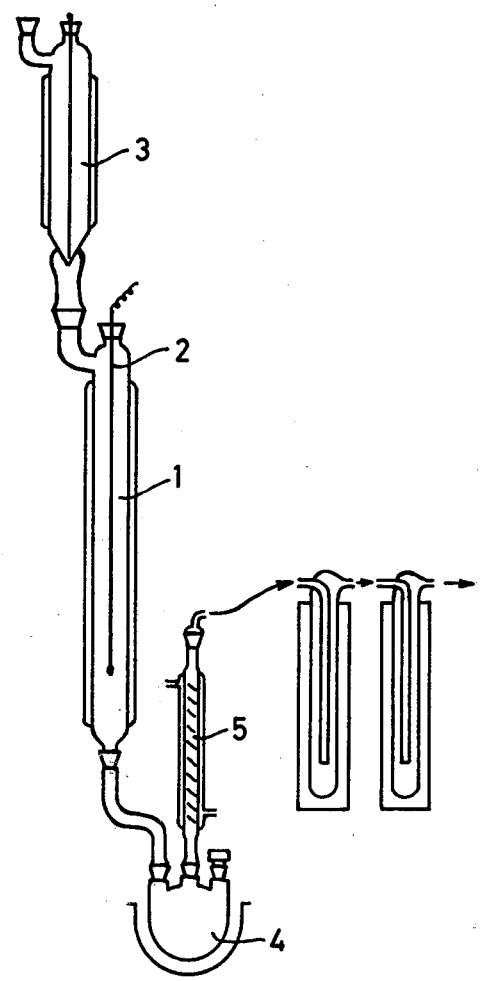

CATALYST FOR THE MANUFACTURE OF TRIETHYLENEDIAMINE

The invention relates to a new catalyst for the manufacture of 1,4-diaza-bicyclo-(2,2,2)-octane (DABCO), also called triethylenediamine, from N,N'-dihydroxyethylpiperazine.

Triethylenediamine

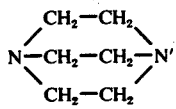

is a very effective catalyst for the manufacture of polyurethanes.

Various methods of synthesis of DABCO are known; eg., it can be synthesized from alkylenepolyamines (ethylenediamine, diethylenetriamine, triethylenetetramine), as disclosed in U.S. Pat. No. 2,937,176 and French Pat. No. 1,218,214.

Other publications propose starting from aminoalcohols (U.S. Pat. No. 2,977,364), mixtures of the above (U.S. Pat. No. 2,977,363) and amine residues (U.S. Pat. Nos. 3,148,190 and 3,231,573).

Processes which start from these materials give only a low yield of triethylenediamine. Better yields are obtained by processes which start from compounds in which a piperazine ring is already present, eg. from N-hydroxyethylpiperazine and N,N'-dihydroxyethylpiperazine (cf. J. Pharm. Soc. Japan 75 (1955), 1370, German Published Application 1,445,578 and U.S. Pat. No. 3,166,558), or N-aminoethylpiperazine (U.S. Pat. No. 2,985,658).

The above processes are in general carried out as gas phase reactions using a fixed bed catalyst. Occasionally, eg. in German Pat. No. 1,132,137, reactions in the liquid phase have been disclosed; however, these take place exceptionally slowly and produce large amounts of residues.

According to the art, only a limited category of catalysts is suitable for the manufacture of triethylenediamine. These are, essentially, synthetic or natural aluminosilictes aluminosilicates used to catalyze petrochemical cracking reactions. Mineralogically, these catalysts belong to the group of the montmorillonites, kaolinites, bentonites and zeolites. Processes based on metal phosphates (U.S. Pat. Nos. 3,172,891 and 3,297,701, German Published Application No. 1,570,004 and French Pat. No. 1,381,243) and tungsten oxide catalysts (U.S. Pat. No. 3,056,788) have also been disclosed. Aluminosilicates are the most commonly disclosed catalysts; they can also be used in alkaline modifications, as mentioned in U.S. Pat. No. 3,120,526, though acid silicates of the above type are mentioned more frequently.

Ishiguro et al., J. Pharm. Soc. of Japan 75 (1955), 1370, use a silicon oxide/aluminum oxide co-precipitate for the manufacture of triethylenediamine.

In general, the starting materials are passed as a vapor over the catalysts at from 200° to 600° C. The addition of inert gases, eg. hydrogen, nitrogen, ammonia and steam, or the use of reduced pressure, has in some publications been regarded as advantageous.

It is true that U.S. Pat. No. 3,157,657 discloses a process for the catalytic manufacture of C-substituted triethylenediamines with pure aluminum oxide as the catalyst. However, this publication expressly points out, and also shows by means of an example (2), that aluminum oxide is unsuitable for the manufacture of unsubstituted triethylenediamine from N-aminoethylpiperazine or N-hydroxyethylpiperazine and that therefore this catalyst can only be used successfully for the manufacture of the C-substituted triethylenediamines from the corresponding monohydroxyethylpiperazines or aminoethylpiperazines. An experimental check of the above information does in fact show that reaction of N-aminopiperazine or N-hydroxyethylpiperazine over aluminum oxide gives a very low yield of triethylenediamine. Large amounts of piperazine are formed and, as is known, this makes it much more difficult to isolate triethylenediamine in a form which is pure, according to its melting point.

It is an object of the present invention to provide a catalyst by means of which triethylenediamine can be manufactured from N,N'-dihydroxyethylpiperazine in the gas phase, in better yield or more rapidly than hitherto.

It is a further object of the invention to provide a catalyst which is simple to procure.

We have found that these and other objects are achieved if triethylenediamine is manufactured by eliminating glycol from N,N'-dihydroxyethylpiperazine and cyclization, in the gas phase, using $Al_2O_3$ as the catalyst.

Using this process, practically complete conversion proves possible so that the reaction product is free from dihydroxyethylpiperazine and monohydroxyethylpiperazine, as well as from piperazine itself. In particular, the absence of piperazine very greatly facilitates working-up. Working-up may comprise, eg., fractional distillation of the reaction product, the fraction which passes over at from 150° to 200° C being collected and subsequently recrystallized. After washing and drying, white crystals which are pure, according to the melting point, are obtained.

The advantages of the process of the invention are thus not only the complete conversion, and the particularly high yield of triethylenediamine, but also the greatly simplified working-up. These advantages are achieved by specifically matching a particular starting material (N,N'-dihydroxyethylpiperazine) with a suitable catalyst ($Al_2O_3$). Evidence of the particular difficulties which are presented by complete separation of piperazine from triethylenediamine is provided by numerus publications and inventions which relate only to the working-up process and in some cases propose expensive separation operations. In this context, attention is drawn to U.S. Pat. Nos. 2,979,506, 2,950,282, 3,120,525 and 3,045,018, German Pat. No. 1,219,491 and British Pat. No. 902,073.

The catalyst used for the process of the invention is crystalline aluminum oxide, which may be modified with suitable metal oxides. Synthetic γ-aluminum oxide, in its commerical formulation, has proved particularly effective. α-, β- and ε-aluminum oxide may also be used; their effectiveness persists if aluminum oxides to which minor amounts (up to 10 percent by weight, and especially from 5 to 10 percent by weight) of suitable additives, such as thorium oxide, chromium oxide, vanadium oxide or the like, eg. oxides of molybdenum, tungsten, manganese, zirconium or hafnium, have been added, are used.

The reaction is carried out in the gas phase, under normal pressure, reduced pressure or slightly superatmospheric pressure. A suitable pressure range is, e.g., from 0.001 to 10 bars. It is particularly advantageous to use a pressure slightly below atmospheric pressure, because this facilitates the vaporization of the piperazine derivative. For example, a pressure of from 0.1 to 0.9 bar may be used with advantage. The catalyst should not come into contact with liquid dihydroxyethylpiperazine, to avoid the deposition of residues. Dihydroxyethylpiperazine vaporizes, eg., at from 150° to 450° C, especially from 250° to 450° C, depending on the pressure conditions. The vaporization is effected in a zone which does not contain any catalyst and is upstream from the catalyst bed. The catalyst may be a fixed bed or a fluidized bed.

The reaction temperature is in general from 200° to 550° C, preferably from 300° to 450° C; the rate of introduction of dihydroxyethylpiperazine is suitably so chosen that the throughput is from about 0.2 to 5 g of starting material per g of catalyst per hour. The catalyst may be used for a prolonged period and is occasionally regenerated in a stream of hot air.

EXAMPLE 1

The apparatus shown schematically in the figure may be used to demonstrate the invention on a laboratory scale. The reactor (1) is an electrically heated quartz tube of 80 cm length and 40 mm internal diameter, of which the upper half (vaporizing zone) is filled with 10 mm ceramic rings whilst the lower half (reaction zone) is filled with catalyst. The temperature in the column can be measured by means of a thermocouple (2) which can be moved along the longitudinal axis of the column. The top of the column carries a dropping funnel (3), which can also be heated, for the dihydroxyethylpiperazine. In order to condense the hot gas mixture which issues, the lower end of the furnace is connected to a cool flask (4) surmounted by a reflux condenser (5). In order to isolate volatile constituents from the stream of gas, the flask is followed by two cold traps which are cooled with a mixture of solid carbon dioxide and acetone.

$\gamma$-Aluminum oxide, in the form of 4 mm extrudates, is used as the catalyst for the experiment. In the course of two hours, 696 g of dihydroxyethylpiperazine are reacted at an internal temperature of 350° C and a pressure of 400 mbars. When all the dihydroxyethylpiperazine has been added, the funnel is rinsed with 50 ml of distilled water. The receiver flask contains 675 g of condensate, consisting of a colored aqueous phase and a solid sediment. The cold traps contain a further 41 g of condensate. Analysis by gas chromatography of the combined condensates shows a triethylenediamine content of 35 percent by weight, corresponding to a yield of 56.1%. Monohydroxyethylpiperazine, dihydroxyethylpiperazine and piperazine itself are not detectable by gas chromatography in the reaction product, ie. the conversion is complete.

The crude product is subjected to fractional distillation and the fraction which passes over at from 150° to 200° C is collected and recrystallized from acetone saturated with triethylenediamine. 238 g of product, corresponding to 53.1% of theory, of melting point 157° C are obtained.

EXAMPLE 2

The apparatus described in Example 1 is used. The column, which is half filled with 4 mm extrudates of $\alpha$-aluminum oxide, is charged, in the course of two hours, with 348 g of dihydroxyethylpiperazine, using an internal temperature of 400° C and atmospheric pressure. After all the material has been introduced, the funnel is rinsed with 50 ml of distilled water. 367 g of condensate are obtained and the cold traps contain a further 10 g. Analysis, by gas chromatography, of the combined condensates shows that the crude product contains 30.2 percent by weight of triethylenediamine, corresponding to a yield of 50.9% of theory. According to analysis by gas chromatography, the reaction product does not contain any compounds having a piperazine structure.

EXAMPLE 3

The apparatus described in Example 1 is half-filled with 4 mm extrudates of a catalyst consisting of $\alpha$-aluminum oxide modified with 10% of thorium dioxide. 348 g of dihydroxyethylpiperazine are reacted in the course of two hours at an internal temperature of 400° C and a pressure of 400 mbars. After all the material has been introduced, the funnel is rinsed with 50 ml of distilled water. 390 g of condensate are obtained and the cold traps contain a further 5 g. According to analysis of the combined condensates by gas chromatography, the crude yield is 46% of theory. Compounds having a piperazine structure are no longer detectable, so that conversion has been complete. The crude product is purified as described in Example 1. The yield of pure product is 90 g (40.2% of theory). The white crystals obtained melt at 158° C.

We claim:

1. A process for the manufacture of triethylenediamine which comprises the elimination of glycol from N,N'-dihydroxyethylpiperazine, with cyclization, in the gas phase at a temperature of from 200° to 500° C and a pressure of from 0.001 to 10 bars, over a solid catalyst selected from the group consisting of $\alpha$-Al$_2$O$_3$, $\beta$-Al$_2$O$_3$, $\gamma$-Al$_2$O$_3$, and $\epsilon$-Al$_2$O$_3$.

2. A process as set forth in claim 1, wherein N,N'-dihydroxyethylpiperazine is vaporized at a temperature of 150° to 450° C.

3. A process as set forth in claim 1, wherein the catalyst contains up to 10% by weight, based on aluminum oxide, of one of the following metal oxides: thorium oxide, chromium oxide, vanadium oxide, molybdenum oxide, tungsten oxide, manganese oxide, zirconium oxide and hafnium oxide.

4. A process as set forth in claim 1 wherein the temperature is from 300° to 450° C.

5. A process as set forth in claim 1 wherein the pressure is from 0.1 to 0.9 bar.

* * * * *